US00PP18910P3

(12) United States Plant Patent
Lintott

(10) Patent No.: US PP18,910 P3
(45) Date of Patent: Jun. 10, 2008

(54) ***CHRYSANTHEMUM* PLANT NAMED 'MAGICAL'**

(50) Latin Name: *Chrysanthemum morifolium*
Varietal Denomination: Magical

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 11/698,350

(22) Filed: Jan. 26, 2007

(65) Prior Publication Data

US 2007/0192919 P1 Aug. 16, 2007

Related U.S. Application Data

(60) Provisional application No. 60/763,282, filed on Jan. 30, 2006.

(51) Int. Cl.
*A01H 5/00* (2006.01)

(52) U.S. Cl. ..... Plt./288

(58) Field of Classification Search ..... Plt./288
See application file for complete search history.

(56) References Cited

PUBLICATIONS

Royal Van Zanten Gardenmum Catalog 2002 listing variety 'Syllabub' at p. 8 with a photograph at p. 11. Catalog released Oct. 23, 2001.

Royal Van Zanten 2003–2004 "Pot plants and Bedding plants" Catalog listing variety 'Mermaid' with a photograph at p. 26. Catalog published Sep. 1, 2003.

*Primary Examiner*—Annette H Para
(74) *Attorney, Agent, or Firm*—Winston & Strawn, LLP

(57) ABSTRACT

A new variety of *Chrysanthemum* plant named 'Magical', having a domed canopy of white quilled decorative flowers and round habit.

1 Drawing Sheet

Latin name of the genus and species: Botanical classification: *Chrysanthemum morifolium.*

Variety denomination: The new *Chrysanthemum* variety denomination is 'Magical'.

BACKGROUND OF THE INVENTION

The present invention comprises a new and distinct cultivar of *Chrysanthemum* botanically known as *Chrysanthemum morifolium,* and referred to by the cultivar name 'Magical'.

'Magical', identified as 31700-0 originated from a cross made in a controlled breeding program in Chichester, West Sussex, United Kingdom. The female parent of the new variety is an undistributed, unpatented seedling identified as '30325-0' and the male parent is the unpatented variety known as 'Syllabub'. The new variety 'Magical' has been asexually reproduced by vegetative cuttings in Chichester, West Sussex, United Kingdom and the distinguishing characteristics are retained through successive generations of asexual reproduction.

BRIEF SUMMARY OF THE INVENTION

'Magical' is a garden type of *Chrysanthemum* plant variety having a domed capitulum of white quilled petalled decorative type flowers.

Comparison with Female Parent

Plants of the new *Chrysanthemum* variety 'Magical' are dissimilar to the female parent '30325-0' in plant habit and growth rate. In side-by-side comparisons in Chichester, West Sussex, United Kingdom, under commercial practice, plants of the new *Chrysanthemum* variety 'Magical' differed from plants of the female parent '30325-0' in the following characteristics:

1. The new variety 'Magical' produces small to medium sized white quilled petalled, slightly upright decorative type flowers whereas the female parent '30325-0' produces large white incurving quilled decorative type flowers.
2. Plants of the new variety 'Magical' have smaller and shorter inflorescence than plants of the female parent '30325-0'.
3. Plants of the new variety 'Magical' have a longer natural season response time than plants of the female parent '30325-0'.

Comparison with Male Parent

Plants of the new *Chrysanthemum* variety 'Magical' are dissimilar to the male parent 'Syllabub' in plant habit and growth rate. In side-by-side comparisons in Chichester, West Sussex, United Kingdom, under commercial practice, plants of the new *Chrysanthemum* variety 'Magical' differed from plants of the male parent 'Syllabub' in the following characteristics:

1. The new variety 'Magical' produces white quilled petalled decorative type flowers whereas the male parent 'Syllabub' produces purple quilled petalled anemone type flowers.
2. Plants of the new variety 'Magical' have smaller and shorter inflorescence than plants of the male parent 'Syllabub'.

3. Plants of the new variety 'Magical' have a shorter natural season response time than plants of the male parent 'Syllabub'.

Comparison with 'Mermaid'

Plants of the new *Chrysanthemum* variety 'Magical' are similar to plants of the unpatented variety 'Mermaid' in plant habit and growth rate. However, in side-by-side comparisons in Chichester, West Sussex, United Kingdom, under commercial practice, plants of the new *Chrysanthemum* variety 'Magical' differed from plants of 'Mermaid' in the following characteristics:

1. The new variety 'Magical' produces white quilled petalled, slightly upright, decorative type flowers whereas 'Mermaid' produces white slightly reflexing flat petalled decorative type flowers.
2. Plants of the new variety 'Magical' have smaller and shorter inflorescence than plants of 'Mermaid'.
3. Plants of the new variety 'Magical' have a longer natural season response time than plants of 'Mermaid'.

BRIEF DESCRIPTION OF ILLUSTRATIONS

Typical specimens of the plant and flowers for the new *Chrysanthemum* variety 'Magical' are shown in the accompanying digital photograph. The colors shown are as true as possible within the usual limits of this kind of illustration.

FIG. 1 is a whole plant view of the new variety 'Magical' grown in a pot. The plant shown in the illustration and described below is 70 days from planting outdoors natural season.

DETAILED BOTANICAL DESCRIPTION

The following description of the new *Chrysanthemum* variety 'Magical' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 50° F. to 70° F. during the day the day under natural light conditions. The plants were grown outdoors in 4 liter pots using a loamless compost. No growth retardants were used. To produce a commercial product, the plants may be pinched once with the center bud removed. The typical container size for commercial growth is 4 liter. It has been observed that the shelf life of the new variety is about 25 days with a response time of about 10 weeks natural season. The new variety is suitable for growth in a temperature range of about 50° F. to 70° F. The new variety may be produced as a garden pot plant. The following description is with respect to a plant produced as pot plant. In the description of this new *Chrysanthemum* variety, color values have been taken from the Royal Horticultural Society Colour Chart (R.H.S.C.C.)

Plant

Plant type: Pot.
Habit: Free branching and spreading.
Height: 40 cm–55 cm.
Width: 40 cm–50 cm.
Stem:
*Length.*—7 cm–10 cm.
*Diameter.*—0.5 cm–0.7 cm.
*Texture.*—Smooth slightly pubescent.
*Color.*—Near 152C.
Branching characteristics: Free branching and spreading.
Lateral branches:
*Length.*—8 cm–11 cm.
*Diameter.*—0.5 cm–0.8 cm.
*Texture.*—Slightly rough.
Number of breaks from pinch: 7–12.
Response time: near 70 days natural season.
Vigor: Medium.
Shelf life: near 25 days.
Life of blooms: near 25 days.
Disease (susceptibility/resistance observed): None observed to date.
Pest (susceptibility/resistance observed): None observed to date.
Drought and temperature (susceptibility/resistance observed): None observed to date.
Growth retardant type and treatment: No treatment necessary.
Propagation:
*Type.*—Vegetative propagation via stem cuttings.
*Time to rooting.*—14 days with soil temperatures of 70° F.
*Rooting habit.*—After 7 Long Days (20 hours of light), the first roots emerge and form root primordia. In 14 Long Days, a complete root system is developed.

Foliage

Number of leaves per lateral branch: 7–9.
Compound or single: Single.
Arrangement of leaves: Alternate.
*Shape of leaf.*—Typically 5 lobed ovate.
*Size of leaf.*—Width: 2.5 cm–5 cm. Length: 4.5 cm–7.5 cm.
*Leaf apex.*—Acute.
*Base.*—Obtuse.
*Attachment.*—Petioled.
*Aspect.*—Slightly undulating.
*Margin.*—Palmately lobed.
*Surface characteristics.*—Top Smooth. Bottom: Slightly pubescent.
Petiole:
*Color.*—Near 146B.
*Length.*—1 cm–2 cm.
*Diameter.*—0.2 cm–0.4 cm.
*Surface.*—Slightly pubescent.
Venation: Net. Prominent mid vein and laterals at underside.
*Color.*—Upper side: near 146C. Under side: near 146C.
Color:
*Mature Leaf, upper side.*—Near 147B; under side: near 147C.
*Young leaf, upper side.*—Near 147B; under side: near 147C.

Flower

Flower appearance: Matte.
Flower type: Quilled decorative.
Flower form: Slightly upright.
Flower shape: Round.
Flowering habit: Cyme.
Number of blossoms per branch: 5–8.

Typical and observed flowering season: natural season September/October.
Inflorescence form: Corymibiform
*Depth of fully expanded blossoms* (*cm*).—3.
*Diameter of fully expanded blossoms* (*cm*).—4–5.
Phyllaries:
*Number.*—20–22.
*Color.*—Near 138A.
*Length.*—0.8 cm–1.1 cm.
*Width.*—0.15 cm–0.2 cm.
*Texture/Appearance.*—Pubescent.
Pedicel:
*Length.*—Terminal: 3.5 cm–6.5 cm; lateral: 4.5 cm–8 cm.
*Diameter.*—0.4 cm–0.7 cm.
*Color.*—Near 138A.
*Angle from the stem* (*degrees*).—Near 25°.
*Surface.*—Slightly rough and pubescent.
*Habit.*—Slightly curving.
*Strength.*—Strong.
Ray florets:
*Form/Shape.*—Quilled.
*Texture/Appearance.*—Matte.
*Number per flower.*—165–180.
*Length.*—1.5 cm–3.0 cm. Width: 0.25 cm–0.5 cm.
*Apex.*—Slightly dentate.
*Base.*—Tubular.
*Margin.*—Entire.
Disc florets: No disc florets.
Fragrance: None.
Flower bud (at onset of color):
*Length.*—1 cm.
*Diameter.*—0.9 cm.
*Form/Shape.*—Globular.
General flower color:
1. *Ray florets, upper side.*—Immature: near 155C. Mature: near 155B. Older/Fading: near 155B.
2. *Ray florets, under side.*—Immature: near 155C. Mature: near 155B. Older/Fading: near 155B.
3. *Bud* (*at onset of color*).—Near 181A.

Flower progression with age: Flowers do not pink with age.
Other distinguishing characteristics: Good weather resistance.

Reproductive Organs

Gynoecium present on Ray florets.
Ray florets per individual flower: Pistillate.
*Pistil number.*—50–60 observed.
*Stigma color.*—Near 144D.
*Stigma shape.*—Forked.
*Style color.*—Near 144D.
*Style length.*—1.2 mm–1.8 mm.
Androecium: Not observed.
Fruit and seeds: None observed.

What is claimed is:

1. A new and distinct variety of *Chrysanthemum* plant, substantially as described and illustrated herein.

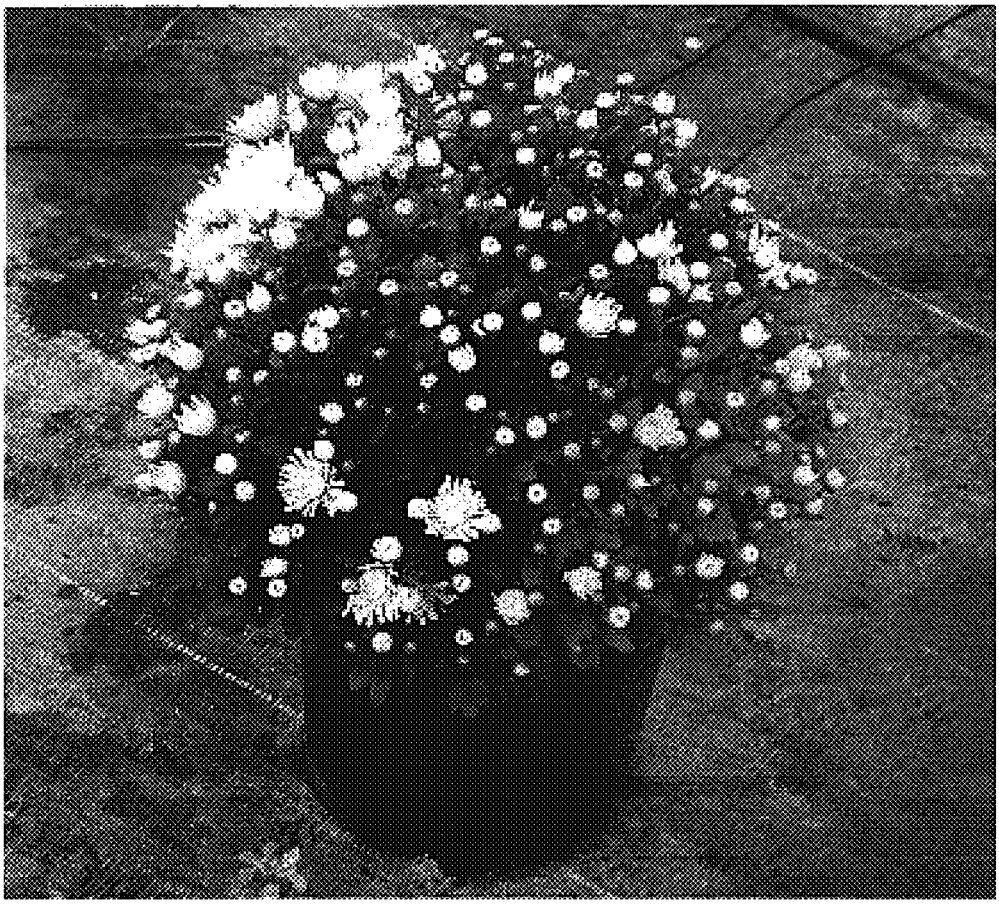

* * * * *